United States Patent [19]

Rodriguez et al.

[11] 4,169,125
[45] Sep. 25, 1979

[54] MODULAR CHEMICAL ANALYSIS SYSTEM

[75] Inventors: Rodolfo R. Rodriguez, Columbia; Eugene K. Achter, Gaithersburg, both of Md.; Carlton D. Deaton, Garden Grove, Calif.; Herbert Goldsmith, Rockville; Horton E. Dorman, Silver Spring, both of Md.

[73] Assignee: Baxter Travenol Laboratories, Inc., Deerfield, Ill.

[21] Appl. No.: 787,625

[22] Filed: Apr. 14, 1977

[51] Int. Cl.² ............... G01N 33/16; G01N 21/24
[52] U.S. Cl. .................... 422/65; 134/22 R; 356/39; 364/497; 422/67; 422/68; 422/105
[58] Field of Search ............ 23/253 R, 259, 230 R; 134/22 R; 364/497; 356/39

[56] References Cited

U.S. PATENT DOCUMENTS

| | | | |
|---|---|---|---|
| 3,489,521 | 1/1970 | Buckle et al. | 23/253 R |
| 3,728,079 | 4/1973 | Moran | 23/253 R |
| 3,753,657 | 8/1973 | Downing et al. | 23/253 R |
| 3,883,305 | 5/1975 | Hoskins et al. | 23/253 R |
| 3,901,656 | 8/1975 | Durkos et al. | 23/253 R |
| 3,917,455 | 11/1975 | Bak et al. | 23/253 R |
| 3,985,508 | 12/1976 | Williams | 23/253 R |
| 4,052,161 | 10/1977 | Atwood et al. | 23/253 R |
| 4,058,367 | 11/1977 | Gilford | 23/259 |

Primary Examiner—R. E. Serwin
Attorney, Agent, or Firm—Henry W. Collins; Joseph T. Downey; Thomas R. Vigil

[57] ABSTRACT

The modular chemical analysis system includes a first module or sample preparation apparatus for preparing sample solutions, a second module including a nephelometer apparatus comprising a stationary flow cell, mechanisms for moving sample solutions into and out of the flow cell, light generating means for passing light through the flow cell, electric circuitry for sensing the relative light scattered (R.L.S.) by the solution or particles in the solution in the flow cell and a third module comprising a microprocessing/calculator having a tape cartridge program. The microprocessor is coupled to the nephelometer apparatus (and, if desired, is also coupled to the sample preparation apparatus) for controlling operation of the nephelometer apparatus (and, if desired, to control the sample preparation apparatus). Also, the output from the nephelometer apparatus is coupled to the microprocessor which receives R.L.S. values and known concentration values for some solutions from which R.L.S. values were obtained. The microprocessor then calculates curve fit parameters for a polynomial regression curve equation, performs a Newton-Raphson inversion on the equation and calculated parameters to automatically calculate concentration values for R.L.S. values obtained from unknown test solutions thereby to obtain calculated concentration values from R.L.S. measurements.

24 Claims, 9 Drawing Figures

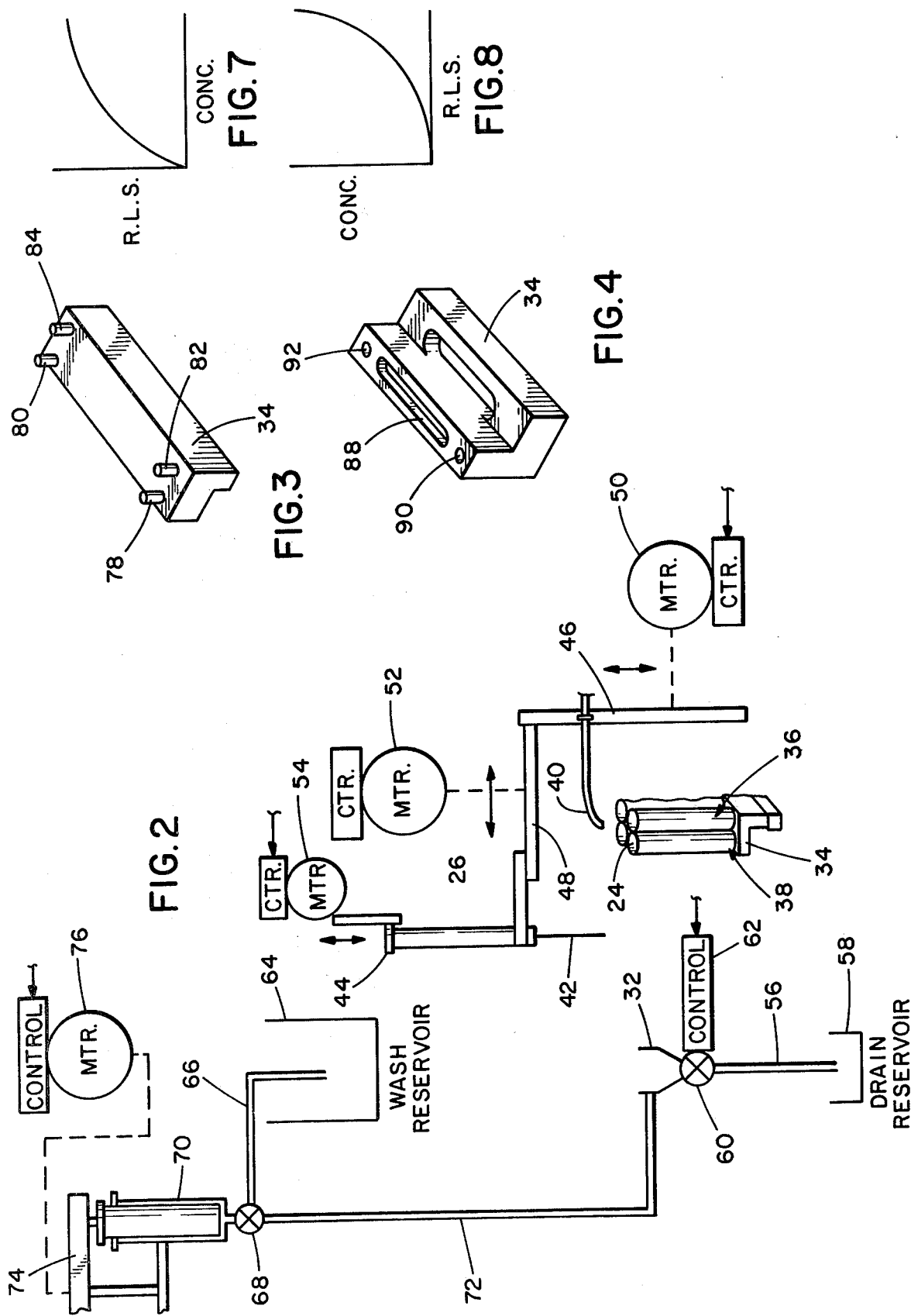

MODULAR CHEMICAL ANALYSIS SYSTEM

BACKGROUND OF THE INVENTION

1. Field of the Invention

The present invention relates to a modular chemical analysis system. More specifically, the field of the invention is an improved automatic nephelometer apparatus and a sampling apparatus for preparing sample solutions to be processed by the nephelometer apparatus.

2. Description of the Prior Art

Heretofore, various automatic and semi-automatic chemical analysis systems have been proposed which typically utilize light absorbance measurement techniques.

Also, heretofore, there have been proposed nephelometer apparatus which operate on the basis of measuring scattered light when a light beam or laser beam is passed through a sample solution. Such previously proposed nephelometer apparatus included a cuvette with a sample therein which was inserted by hand into a measuring block, the light scatter measurement then being performed, followed by removing the cuvette by hand to insert another cuvette with a sample solution therein. Since this was done manually, it took some time to perform.

Also, heretofore, transporters have been proposed for transporting sample cup cartridges having five sample cups therein in a continuous horizontal path.

As will be described in more detail hereinafter, the modular chemical analysis system and the apparatus comprising some of the present invention enable one to use standard transporters and an existing nephelometer portion together with a known microprocessor to automatically prepare sample solutions and automatically make relative light scatter measurements followed by automatic calculations of the concentration of a substance being assayed from the relative light scattered measurements. In this way a quicker and more efficient processing of sample solutions, typically blood serum solutions, is made to determine concentrations of various substances such as proteins, antibodies, etc., in the blood serum.

SUMMARY OF THE INVENTION

According to the invention there is provided a modular chemical analysis system including a first module for preparing sample solutions, a second module including a nephelometer apparatus comprising a stationary flow cell and means for moving sample solutions into and out of said flow cell, light generating means for passing light through the flow cell and means for sensing the relative light scattered (R.L.S.) by the solution or particles in the solution in the flow cell and a third module comprising a microprocessor/calculator having a tape cartridge program and being coupled to said first module and said second module for controlling operation of said first module and said second module and for receiving R.L.S. values and known concentration values of those solutions from which R.L.S. values were obtained, calculating curve fit parameters for a polynomial regression curve equation and utilizing said equation and calculated parameters to automatically calculate concentration values for R.L.S. values obtained from unknown test solutions thereby to obtain calculated concentration values from R.L.S. measurements.

Further according to the invention there is provided a sample solution preparation apparatus comprising a sample preparation station, a transporter for transporting sample cup cartridges, each having a plurality of sample cups therein, past said sample preparation station a given number of the sample cups having a sample liquid therein and an equal number of empty cups being aligned therewith, means for metering a given amount of diluent or reagent and for dispensing same at said sample preparation station into selected ones of the empty sample cups, means for withdrawing a precise minute amount of sample liquid from each of those cups having sample liquid therein at said sample preparation station and for dispensing said precise minute amount of said sample liquid into selected ones of the empty sample cups aligned therewith, means for cleaning said sample liquid withdrawing and dispensing means between dispensings of sample liquid, and control means for controlling said apparatus by causing indexing of said transporter, operation of said metering and dispensing means, operation of said sample liquid withdrawing and dispensing means and operation of said cleaning means at predetermined times and in a predetermined sequence.

Still further according to the invention there is provided an automatic nephelometer apparatus comprising a sampling station, a transporter for transporting sample cup cartridges in a predetermined path past said sampling station, each cartridge having a plurality of sample cups therein, means for withdrawing a quantity of sample solution from one of the sample cups at said sampling station, a flow cell, means fluidly coupled to said flow cell for moving the quantity of sample solution into said flow cell, means for passing light through said flow cell, means for sensing the relative light scattered (R.L.S.) by the sample solution and/or particles in the sample solution and for producing a sample solution value directly related to the R.L.S. sensed by said sensing means, means for identifying each sample solution and for storing such identification with the sample solution value therefor in a memory, means for moving the quantity of sample solution out of said flow cell, means for cleaning said flow cell, and control means for controlling operation of said apparatus by controlling indexing of said transporter, operation of said withdrawing means, operation of said moving means, operation of said sensing means, operation of said cleaning means and operation of said identifying and storing means at predetermined times and in a predetermined sequence.

BRIEF DESCRIPTION OF THE DRAWINGS

FIG. 2 is a fragmentary schematic view of a movable syringe mounted on said sample preparation apparatus, a wash fluid system associated with the sample preparation apparatus and a pair of aligned sample cup cartridges mounted on an adapter.

FIG. 3 is a perspective view of the adapter shown in FIG. 2 in an upright position.

FIG. 4 is a perspective view of the adapter shown in FIG. 3 but rotated 180° to an overturned position;

FIG. 7 is a graph of relative light scattered (R.L.S.) obtained when light is passed through a sample solution in the flow cell of the nephelometer apparatus plotted on the Y coordinate and the concentration value corresponding to the R.L.S. value plotted on the X coordinate.

FIG. 8 is a graph which is an inversion of the graph shown in FIG. 7 and which has the concentration value on the Y coordinate and the corresponding R.L.S. value on the X coordinate.

DESCRIPTION OF THE PREFERRED EMBODIMENTS

Figure 1:
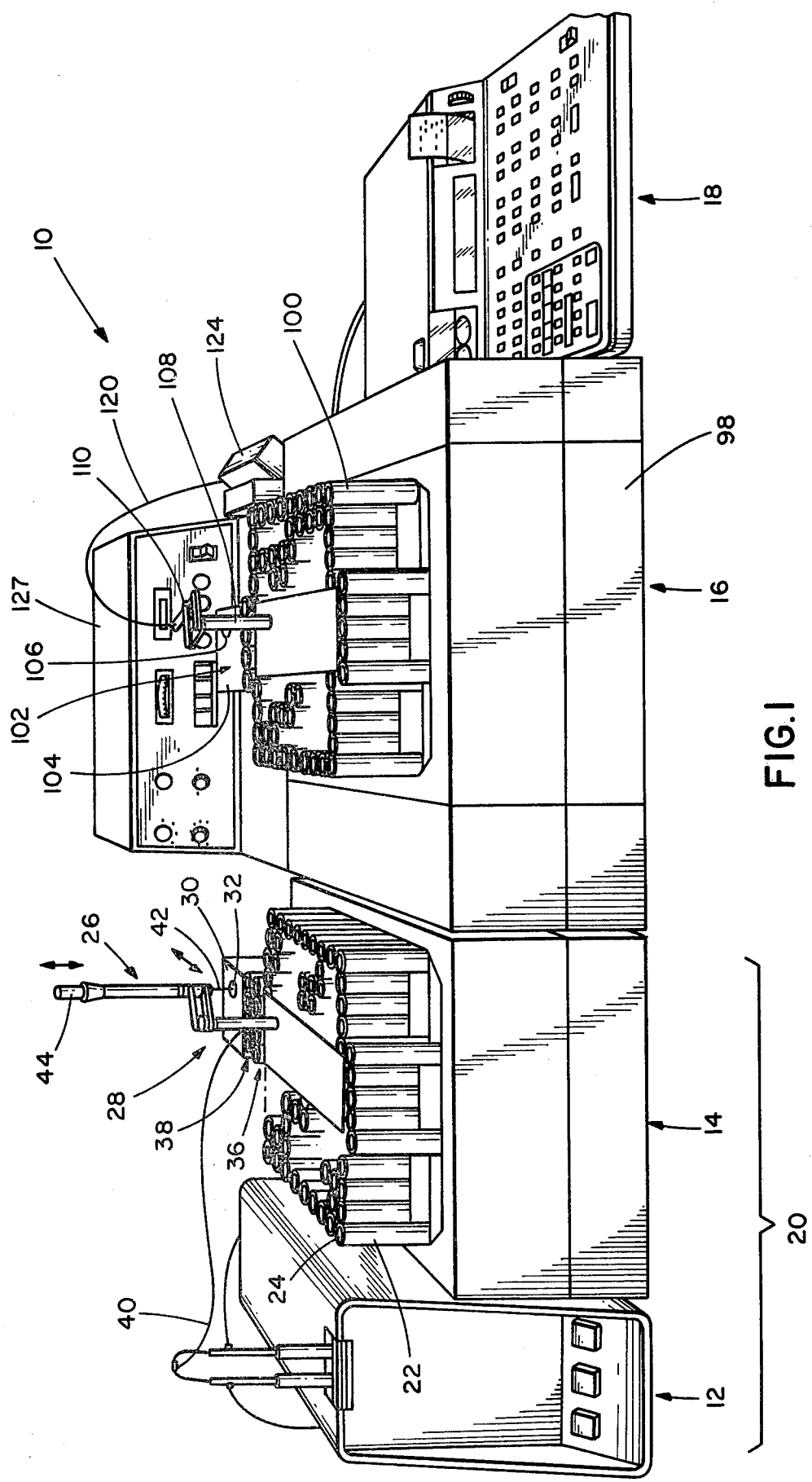
FIG. 1 is a perspective view of a modular chemical analysis system comprising a sample preparation apparatus, a nephelometer apparatus and an associated microprocessor/calculator.

Referring now to the drawings in greater detail there is illustrated in FIG. 1 a modular chemical analysis system generally identified by reference numeral 10. The system 10 includes a microdiluter apparatus 12 which can be a Hyland Micro Diluter ™ sold by Hyland, a division of Baxter Travenol Laboratories, Inc., 3300 Hyland Avenue, Costa Mesa, Calif. 92626. The system 10 further includes a diluter transporter 14 which together with the microdiluter 12 comprise a first module of the system 10, a nephelometer apparatus 16 comprising a second module of the system 10 and a microprocessor/calculator 18 associated with the nephelometer apparatus 16 and comprising a third module of the system 10.

The microdiluter 12 and the diluter transporter 14 and associated mechanisms to be described hereinafter comprise a sample preparation apparatus generally identified herein by reference numeral 20.

With the chemical analysis system 10 of the present invention, an operator can substantially automatically prepare various types of test and blank solutions with the sample preparation apparatus 20 and then process those test and blank solutions in the nephelometer apparatus 16. The processing is done automatically by the nephelometer apparatus 16 and does not require insertion and removal of cuvettes containing test solutions or blank solutions since the nephelometer apparatus 16 includes a stationary flow cell as will be described in greater detail hereinafter.

The microprocessor/calculator 18 is connected to the nephelometer apparatus 16 not only for controlling operation thereof but also for receiving relative light scattered measurement values (hereinafter referred to as R.L.S. values) from test solutions and blank solutions for calculating the parameters for a polynomial equation defining the curve of concentration versus R.L.S. for different concentrations of the substance being assayed in an test solution. Once the parameters of the equation are determined, R.L.S. values from unknown test solutions having an unknown concentration of a substance therein when known amounts of a reagent are inserted into the unknown test solution can be plugged into the equation by the microprocessor/calculator 18 to obtain a rapid calculation of the concentration value of the substance being assayed.

Basically there are four solutions which need to be prepared. The first solution is a reference blank solution which contains a known liquid sample having a known concentration of a substance to be assayed mixed with a predetermined amount of diluent. The second solution is an unknown blank solution having an unknown liquid sample having an unknown concentration of the substance to be assayed mixed with a predetermined amount of diluent. The third solution is a reference test solution having a known liquid sample with a known concentration of the substance to be assayed mixed with a predetermined amount of reagent. The fourth solution is an unknown test solution comprising an unknown liquid sample with an unknown concentration of the substance to be assayed and a predetermined amount of reagent. All of these test solutions can be prepared with the sample preparation apparatus 20.

The transporter 14 is of known type and includes a conveyor mechanism hidden from view in FIG. 1 on which a plurality of sample cup cartridges 22 are carried. Each cartridge 22 has five aligned sample cups 24 therein.

According to the teachings of the present invention, and with reference to FIGS. 1 and 2, the transporter 14 has a syringe mechanism 26 mounted thereon which defines a sample station 28 along the path of travel of the cartridges 22 in a closed path on the transporter 14. Adjacent the sample station 28 is located a wash station 30 including a wash bowl 32. The wash bowl 32 and the wash station 30 form part of a cleaning mechanism for cleaning off a probe on the syringe mechanism 26.

In accordance with the teachings of the present invention, an adapter 34 (FIGS. 2, 3 and 4) is detachably mounted on the conveyor for supporting two cartridges 22 in parallel aligned relationship such that each sample cup 24 in one cartridge is aligned with a similar sample cup 24 in the other cartridge 22. In this way, a pair of aligned cartridges 22 can be moved past the sampling station 28 when the conveyor mechanism would normally move one sample cup cartridge 22 past the sampling station 28. Details of construction of the adapter 34 are set forth below.

One of the rows of sample cups 24 in one of the cartridges identified by reference numeral 36 has each sample cup therein filled with a sample of blood serum. Each one of the aligned sample cups in the row of sample cups in the other cartridge, generally identified by the reference numeral 38, is adapted to receive the components for a particular solution to be prepared which will consist of a precise minute amount of known serum and a predetermined amount of diluent, a precise minute amount of unknown serum and a known amount of diluent, a precise minute amount of known serum and a known amount of antiserum or a precise minute amount of unknown serum and a known amount of antiserum. The microdiluter 12, which is of known type, has mechanisms therein for dispensing through an outlet tubing 40 a predetermined amount of either antiserum or diluent. Also to maintain the shelf life of the antiserum which is composed of several solutions the diluter 12 is operable to mix the components of the antiserum just prior to delivering them to the transporter 14 via the tubing 40. Also, as shown, the tubing 40 extends to the sampling station 28 and has an open end (not shown) positioned above the row 38 of sample cups and above the path of movement of the sample cups for dispensing a predetermined amount of diluent or antiserum into that row 38 of sample cups.

The syringe mechanism 26 includes a syringe probe 42 and a syringe pump 44. As best shown in FIG. 2 the syringe mechanism 26 is mounted to a post 46 by means of a pantograph mechanism 48. Also as shown in FIG. 2 a motor and control 50 are provided for moving the post 46 upwardly and downwardly, a motor and control 52 are provided for operating the pantograph mechanism 48 to move the syringe probe 42 back and forth between a position over a sample cup in the row 36, a position over the sample cup in the row 38 and a position over the wash bowl 32, and a motor and control 54 for moving the syringe pump 44 upwardly and downwardly.

A system for washing the probe 42 includes the wash station 30 with the wash bowl 32. In addition such system includes a drain conduit 56 connected to the bottom of the wash bowl 32 and draining into a drain reservoir 58. A valve 60 is situated in the conduit 56 and operated by a solenoid control 62. The system also includes a wash fluid reservoir 64 having a conduit 66 extending therein. The conduit 66 is connected at its other end through a valve 68 to a syringe pump 70. The valve 68 is also connected to a conduit 72 leading to the wash bowl 32. The syringe pump 72 is connected to an operating mechanism 74 which is operated by a motor and control 76.

As shown, and if desired, the tubing 40 can be mounted to the upright post 46.

Referring now to FIGS. 3 and 4 the adapter 34 has two pairs of lugs 78, 80 and 82, 84. Each lug is adapted to have received thereon openings at the bottom of one of the sample cup cartridges 22. Also as shown in FIG. 4 each adapter 34 has a lower depending elongate portion 86 which has a width less than the width of the upper portion of the adapter 34 as shown in FIG. 3. The depending elongate portion 86 has an elongate slot 88 therein and a hole 90 and a hole 92 at each end. The slot 88 or holes 90 and 92 are received over lugs on the upper surface of the conveyer such lugs being similar to the lugs 78-82, for detachably securing the adapter 26 on top of the conveyer mechanism of the transporter 14. In this way, and as best shown in FIGS. 1 and 2, a pair of aligned sample cup cartridges 22 with parallel spaced, aligned sample cups 24 are arranged in the two rows 36 and 38.

In the operation of the sample preparation apparatus 20, a control mechanism which can be mounted within the transporter 14 or can consist of the microprocessor 18 is utilized to operate the transporter 14, the syringe mechanism 26 and the washing system including the motor and control 76 and operating mechanism 74 as well as valve 60 and control 62 therefor in the following manner to prepare sample solutions. First of all, for each sample cup 24 in line 38 aligned with a sample cup 24 in the line 36 the diluter 12 can be instructed by the control mechanism to dispense one ml of either diluent or antiserum prepared in the diluter 12 into the selected sample cup from the end of the tubing 40 over that sample cup 24 in line 38. Then the syringe mechanism 26 is operated, i.e., motors and controls 50, 52 and 54 are operated to cause the probe 42 to dip into a sample cup 24 in the line 36 to pick up a precise minute amount of sample, namely, a $\mu$l of serum. This is accomplished by drawing a predetermined length of serum into the syringe probe 42 which has a very small internal diameter by operating the motor and control 54. Then the probe 42 is moved by the motors and controls 50 and 52 over the wash bowl 32 and into the wash bowl 32 to rinse off any serum on the exterior surface of the probe 42. Next the probe 42 is moved over the sample cups 24 in the row 38 and the motor and control 54 is operated to dispense a microliter ($\mu$l) of serum into a selected sample cup in the row 38. In the meantime, the motor and control 76, mechanism 74 and syringe pump 70 have been operated to refill the washbowl 32 after the previous quantity of wash fluid has been drained into the drain reservoir 58. Then the probe 42 is moved over and into the washbowl 32 and dipped therein and wash fluid is drawn into the syringe mechanism 26 and then ejected therefrom into the washbowl 32. At the same time wash fluid is moved by the pump 70 into the washbowl 32 to wash off the exterior of the probe 42.

After this has been accomplished the transporter is indexed to move another sample cup into a sampling position and aligned with a sample cup containing serum so that the above sequence of operations can take place to dispense the desired amount of diluent or antiserum into the selected sample cup 24 and to transfer a microliter of blood serum from another sample cup in the row 36 of sample cups to a sample cup aligned therewith in the row 38.

Once a first empty sample cup is sensed by sensors at the sample preparation station 28, the control mechanism will cause that cup and each successive cup to be filled with a predetermined solution in a predetermined order.

Figure 5:
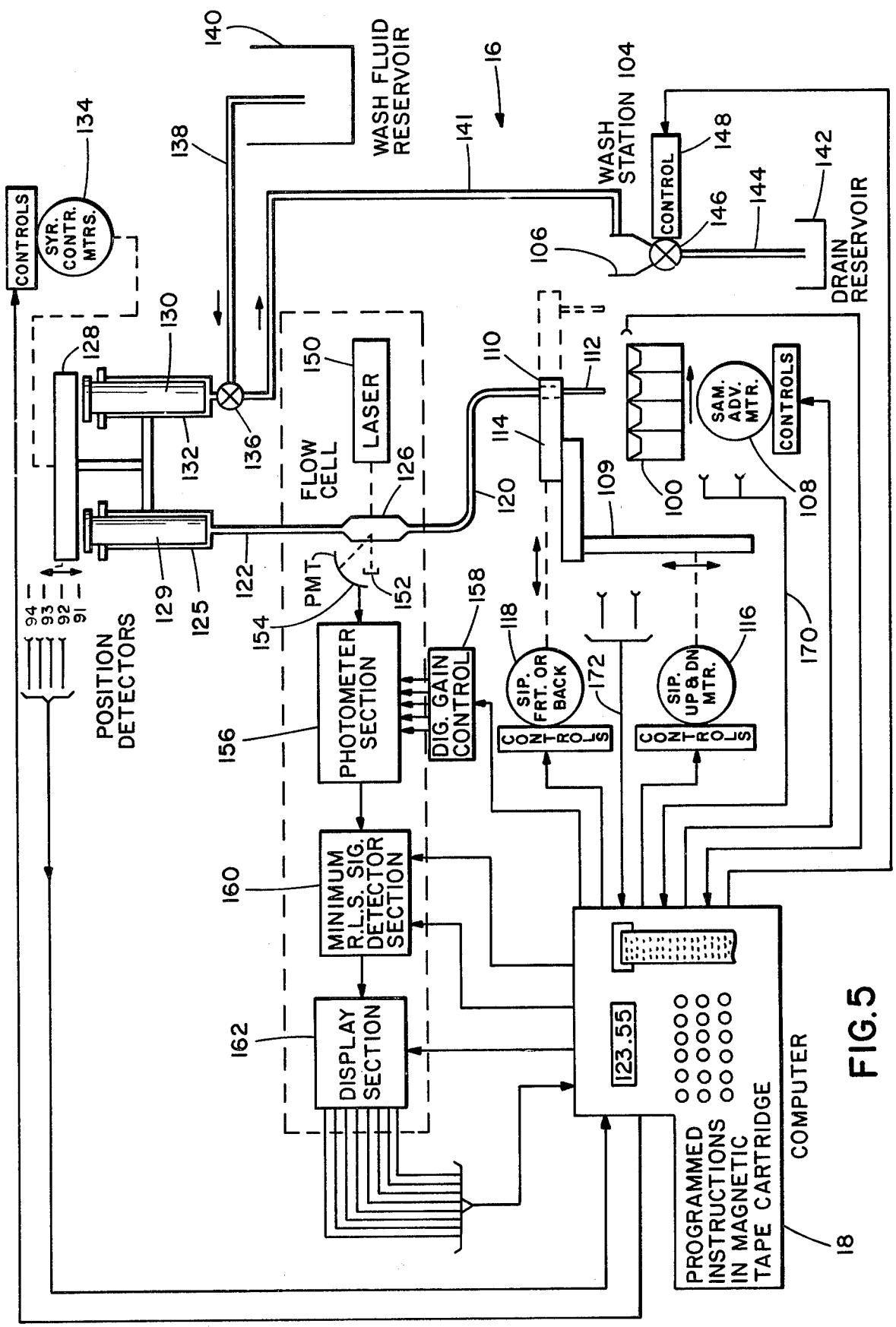
FIG. 5 is a schematic diagram of the nephelometer apparatus.

With reference to FIGS. 1 and 5, the nephelometer apparatus 16 includes a transporter 98 similar to the transporter 14 with a plurality of sample cup cartridges 100 mounted on a conveyer (hidden from view) for movement in a closed path past a sampling station 102 adjacent to which is located a wash station 104 similar to wash station 30 and having a wash bowl 106. The motor and control for indexing or advancing the sample cup cartridges 100 is schematically illustrated in FIG. 5 and identified by reference numeral 108.

Extending upwardly from the transporter 98 is a post 109 which mounts a sipper device 110 which includes a probe 112 (FIG. 5) and a pantograph mechanism 114 movably mounting the probe 112 to the post 109.

As best shown in FIG. 5 the sipper device also includes a motor and control 116 for moving the post 109 upwardly and downwardly and a motor and control 118 for moving the pantograph mechanism 114 back and forth to move the probe 112 from a position over a sample cup in one of the cartridges 100 to a position over the wash bowl 106.

As shown in FIGS. 1 and 5 the probe 112 is connected by a conduit 120 to a block 124 mounting (FIG. 1) a flow cell 126 therein. The block 124 forms part of the nephelometer portion 127 of the nephelometer apparatus 16. The nephelometer portion 127 and the block 124 are known pieces of equipment and form no part of the present invention except for the novel flow cell 126 mounted within the block 124 and the novel combination of the nephelometer portion 127 in the nephelometer apparatus 16 and in the modular chemical analysis system 10. The flow cell 126 is a generally cylindrical cuvette with conical tapered end portions one of which is connected to the conduit 120 and the other of which is connected to a conduit 122 leading to a syringe pump 125. The syringe pump 124 has a syringe pump piston 129 which is connected to an operating mechanism 128. This operating mechanism 128 also is connected to another syringe pump piston 130 forming part of a second syringe pump 132. As shown in FIG. 5 the operating mechanism 128 is operable to operate the first and second syringe pumps 125 and 132 in tandem. For this purpose a motor and control 134 are coupled to the operating mechanism 128 and level sensing detectors 91 to 94 are provided for sensing the movement of the operating mechanism 128 and then causing the microprocessor 18 to limit the stroke of up "draw" movement or down "eject" movement of the pistons 126 and 132, as will be explained in greater detail below. The outlet of the pump 130 is connected to a two way valve 136 which has a conduit 138 extending therefrom into a wash fluid reservoir 140. Another conduit 141 is also connected to the valve 136 and extends to the wash bowl 106 at the wash station 104. Beneath the wash bowl 106 is a drain reservoir 142 and a drain conduit 144 is connected through a valve 146 to the wash bowl 106. A solenoid control 148 operates the valve 146.

The nephelometer portion 127 includes a laser 150 for passing light through the flow cell 126 to a light trap 152. The light scattered by the solution and the particles in the solution in the flow cell 126 is picked up by a photomultiplier tube 154 and the relative light scatter signal from the photomultiplier tube is passed to a photometer section 156 having a digital gain control 158 connected thereto. The output from the photometer section 156 is then passed to a minimum R.L.S. signal detector section 160 and from there to a display section 162. The microprocessor calculator 18 is a small computer and typically can be a model 9815A computer manufactured by Hewlett Packard. The computer interfacing or a separate interfacing is connected via the lines extending from computer 18 as shown in FIG. 5 to the various controls which include the motor and control 116, the motor and control 118, the motor and control 108, the solenoid 148, the motor and control 134, the stroke position detectors 91 to 94, the digital gain control 158, the signal detector 160, and the display section 162. Also connected to the computer 18 is a sample cup position sensing line 170 and a syringe position sensing line 172. The sample cup position sensing line 170 tells the computer where each sample cup in the cartridge of the plurality of the cartridges in the transporter 98 is and in what position it is in at the sampling station 104. The computer 18 is programed so that the first sample cup to reach the sampling station 102 will then start the computer to operate the various mechanisms. All subsequent sample cups are then processed in a predetermined order which order information is stored in the computer so that appropriate samplings and identification of samplings can be made.

The syringe position line 170 has sensors at the end which tell the computer 18 at what level the syringe probe 112 is located. In this way, the syringe probe position sensors correlate the position of the syringe probe 112 with the position of the pump pistons 129 and 130.

In the operation of the syringe pumps 125 and 132 the operating mechanism is reciprocated and the stroke detectors limit movement of each pump piston 129 and 130 to one of five pump piston strokes of different lengths. The first stroke is a very short "draw" stroke for aspiration of air into the probe 112. The second stroke is a continuation of the "draw" stroke since the air is drawn into the probe 112 as it is being lowered into one of the sample cups in the cartridge 100. When the probe 112 is immersed into the serum in the cup the second stroke of the piston 129 begins and is a continuation of the first "draw" stroke. The length of the second stroke is sufficient to aspirate sample solution from the sample cup into the probe 112 and up to a predetermined level in the flow cell 126. At the same time the pump 132 is operated to draw a quantity of wash fluid from the reservoir 140 into the pump 132. The third stroke is an "eject" stroke having a length greater than the sum of the first and second stroke lengths for ejecting all the quantity of sample solution from the flow cell 126 and probe 112 back into the sample cup and at the same time to cause the pump 132 to eject wash fluid into the wash bowl 106 at the wash station 104. The fourth stroke is a "draw" stroke and has a length greater the sum of the first and second strokes for aspirating wash fluid into the probe 112 and into the flow cell 126 above the level reached by the quantity of sample solution in the flow cell 126. At the same time, the pump 132 draws wash fluid from the reservoir 140 into the pump 132. The fifth stroke is an "eject" stroke and has a length greater than the fourth stroke to ensure that all of the wash fluid is ejected from the flow cell 126 and probe 112 while at the same time wash fluid is ejected by the pump 132 into the wash bowl 106 and around the lower end of the probe 112 to wash the outside of the probe 112 while the wash fluid inside the probe 112 is ejected into the wash bowl 106.

Figure 6A:
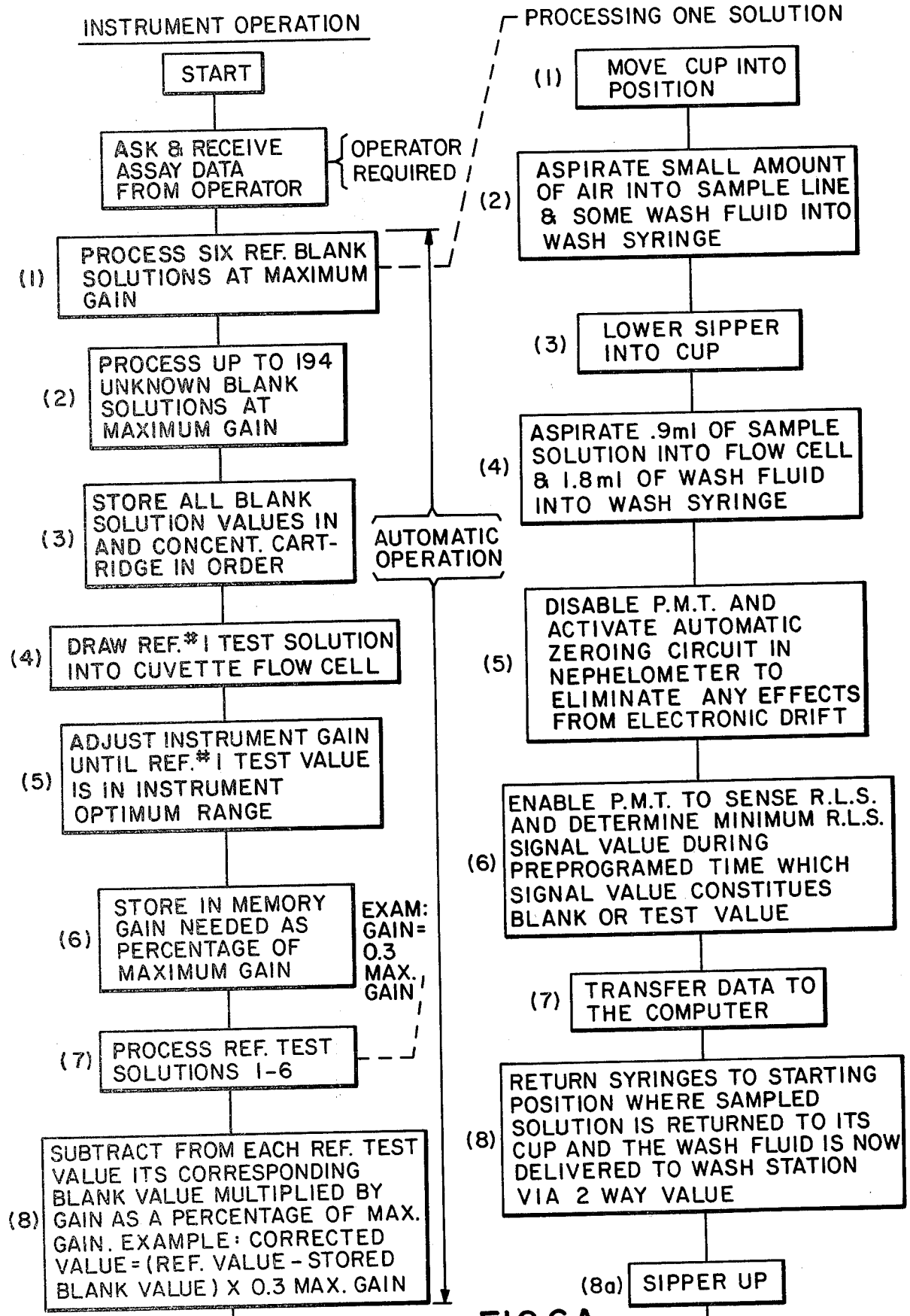
FIGS. 6a and 6b are flow diagrams showing the sequence of operation steps of the nephelometer apparatus and associated microprocessor/calculator.
Figure 6B:
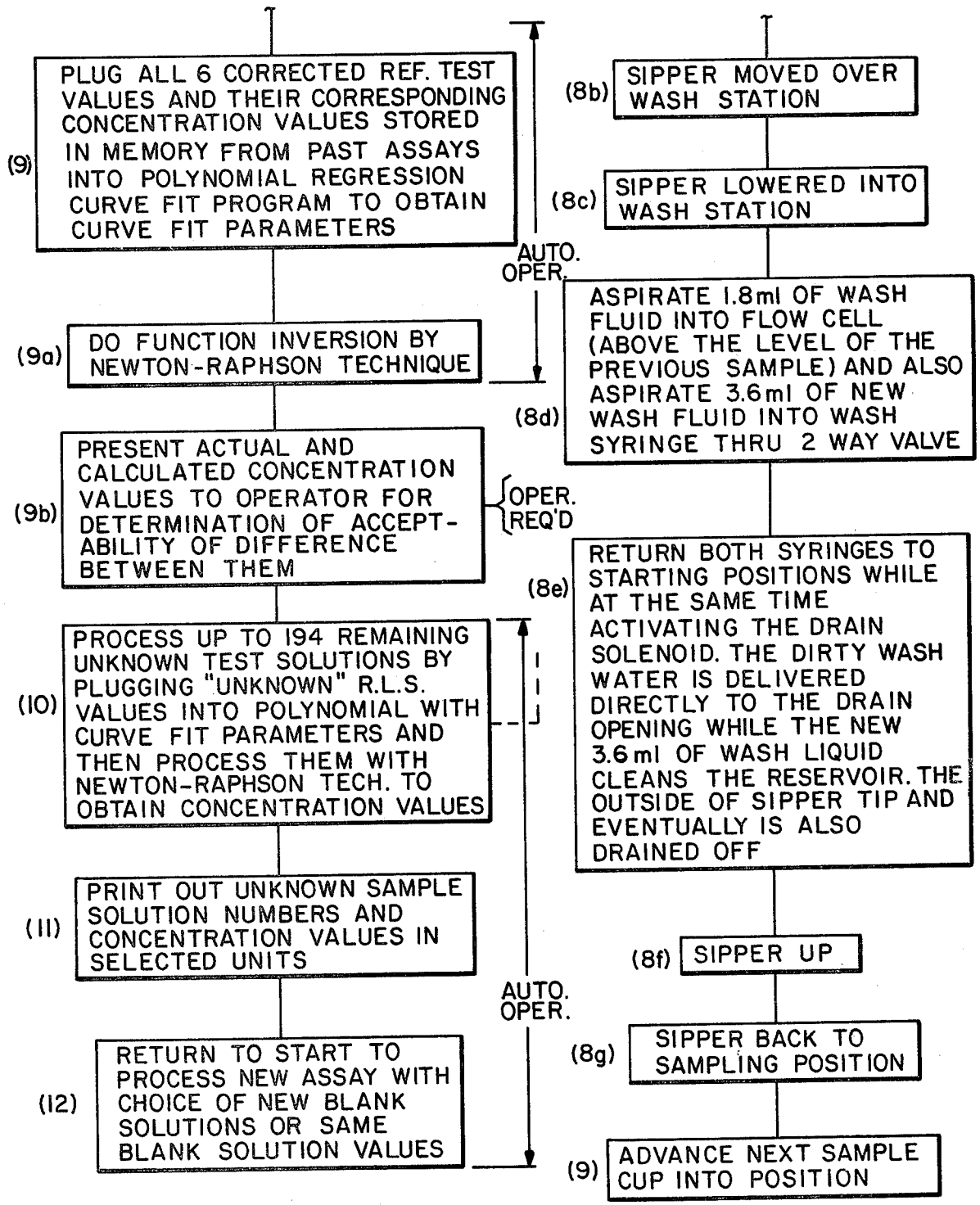

The operation of the nephelometer apparatus 16 in conjunction and with computer 18 will now be described in connection with the flow diagrams shown in FIGS. 6A and 6B. First of all, one procedure or process which is repeated several times in the operation of the apparatus 16 will be described. This process is the processing of one sample solution and takes about 30 seconds to perform. The processing of one sample is controlled, of course, by the programed computer which has electric circuitry therein connected so as to cause the various operation steps. The sequence of operation steps is as follows:

1. Indexing of the transporter 98 to move a selected sample cup into a sampling position at the sampling station 102.
2. Aspiration of a small amount of air into the probe 112. This is accomplished by operating mechanism 128 and moving it a small distance upward. At the same time some wash fluid is drawn into the wash syringe pump 132.
3. Movement of the probe 112 into the sample cup while the pump piston 129 is moving upwardly.
4. Continued movement of the pump piston 126 upwardly to aspirate a predetermined quantity, namely 0.9 milliliters, of sample solution from the sample cup into the flow cell 126. At the same time 1.8 milliliters of wash fluid is drawn into the pump 132.
5. Disabling of the photomultiplier tube 154 to calibrate the measuring circuitry 156, 158, 160, 162 associated therewith. In other words, automatic zeroing circuitry in the nephelometer apparatus is operated to eliminate any effects from electronic drift. This is done in a time period of 3 seconds during which time bubbles in the flow cell 126 migrate to the top of the sample solution in the flow cell 126 and out of the optical path from the laser 150 to the light trap 152.
6. Enabling and operating the photomultiplier tube to sense the relative light scattered (R.L.S.) and to determine the minimum R.L.S. signal values during a preprogrammed time of approximately 3 seconds.
7. Transfer of the identifying number of the sample solutions, the sample solution concentration value, if known, and the R.L.S. value to the computer.
8. Return of the syringe probe to the starting position where the sample solution is returned to the sample cup and wash fluid is delivered to the wash station via the two-way valve 136.
    8a. Movement of the probe 112 of the sipper device 110 upwardly to its upper position.

8b. Movement of the syringe probe 112 horizontally to a position over the wash bowl 106 at the wash station 104.

8c. Lowering of the probe 112 into the wash bowl 106.

8d. Aspiration of 1.8 milliliters of wash fluid into the probe 112 and flow cell 126 above the level reached by the sample solution in the flow cell. Also, 3.6 ml of new wash fluid is drawn into the pump 132 through the two-way valve 136.

8e. Both syringe pumps 129 and 132 are returned to the starting position while at the same time drain solenoid 148 is operated to open the drain valve 146 and allow wash fluid being ejected from probe 112 to drain into the drain reservoir 142. At the same time wash fluid from the pump 132 cleans the outside of the probe and is then drained into the drain reservoir 142.

8f. Movement of the probe 112 to its upper position.

8g. Movement of the probe 112 back to its starting position at the sampling station.

9. Indexing of the transporter 98 to place the next sample cup in a sampling position.

It is noted that by returning the sample solution back to the sample cup an operator can make an antigen excess determination of the serum in the sample cup because none of it is washed or thrown away. In this respect, at a certain peak concentration of antigen in a sample of blood serum the addition of further antigen plus reagent will result in less light scatter because of the solubility of some of the complexes being formed in the solution. By making such an antigen excess determination i.e., adding antigen to the serum and then adding a reagent to see what happens one can determine whether the concentration of antigen in the serum was before or after the point of peak concentration.

In the complete operation of the nephelometer apparatus 16 with the use of the program on the tape inserted into the computer 18, the circuitry in the computer is connected to cause a predetermined sequence of operations to occur after an operator has determined a number of things. First of all, he must determine what blank solutions are going to be utilized. Secondly, he has to determine what units are to be utilized. Thirdly, he has to determine what substance or antigen is to be assayed and what reference solutions are to be utilized. After this has been done the predetermined sequence of operation caused by the circuitry and connections thereof in the computer, steps are performed automatically and comprise the following:

1. The processing of a plurality of (e.g., 6) reference blank solutions in the manner described above for processing one solution and at maximum gain for the photomultiplier tube.
2. Process of a plurality (e.g., 194) of unknown blank solutions at maximum gain with the solution processing steps described above.
3. Storage of all blank solutions values in a memory circuit of the computer in a predetermined order which corresponds to the predetermined identification of the serum in each sample cup.
4. Drawing of a quantity of the first reference test solution into the flow cell 126.
5. Adjusting the gain of the photomultiplier circuitry until the first reference test value measured by the photomultiplier tube 154 is in the operating range of the measuring portion of the photometer section 156.
6. Storing the adjustment in the memory as a percentage of the maximum gain that is needed to place the first reference test value in the optimum range of the measuring portion of the photometer section 156.
7. Process of a predetermined plurality of test solution according to the solution processing steps described above.
8. Causing a substraction from each R.L.S. reference test value of its corresponding R.L.S. blank value in the computer multiplied by the adjustment of gain as a percentage of maximum gain to obtain corrected R.L.S. test values. For example with an adjustment of 0.3 maximum gain one would take the reference value minus the stored blank value times 0.3 maximum gain to obtain the corrected value.
9. Plug all corrected reference test values and their corresponding known concentration values stored in the computer memory from past assays into a polynomial regression curve fit program to obtain curve fit parameters or coefficients.
   9a. Perform a polynomial function inversion by the Newton-Raphson technique.
   9b. Present the actual and calculated concentration values in the form of a print-out to the operator for a determination of the acceptability of the difference between them. If the difference is too great the operator can tell the computer to disregard one particular actual concentration value and recalculate the parameters for the polynomial equation defining the curve without the one concentration value. For example, if six test samples are used and one measurement is unsatisfactory that measurement can be disgarded and a curve defining equation and parameters therefor can be determined using only five measurement values.
10. Process the plurality of unknown test solutions to be assayed using the steps for processing one solution described above to obtain R.L.S. values for each unknown test solution and plug those R.L.S. values into the polynomial regression curve equation with the obtained curve fit parameters followed by processing that equation and data with the Newton-Raphson technique to obtain calculated concentration values of the antigen in the unknown test solution.
11. Causing a print-out of the unknown sample solution numbers and the calculated concentration values for the unknown sample solution numbers.
12. Resetting the nephelometer apparatus 16 and returning the probe 112 to its initial position to ready the nephelometer apparatus 16 for processing a new assay with a choice of new blank solutions or utilizing the same R.L.S. blank solution values stored in the computer memory.

In FIG. 7 is shown a curve of relative light scatter (R.L.S.) versus concentration. With this type of curve where R.L.S.=f (concentration) one can obtain a good curve fit for the R.L.S. data obtained. This function is well represented by a polynomial equation. The inverted function, Concentration=f (R.L.S.) is a more complicated function. Accordingly, with the program in the computer 18 one can obtain R.L.S.=f (concentration) for a good curve fit. Then, according to the teachings of the present invention, the computer 18 uses the Newton-Raphson technique to perform the following operation:

Given R.L.S. = f (concentration) and given a value of R.L.S., obtain a calculated concentration value. With the Newton-Raphson technique, one can easily obtain that value and it is equivalent to reading the concentration off of the inverted curve shown in FIG. 8.

From the foregoing description, it will be apparent that the system 10 and apparatus 14, 16, 18 and 20 of the present invention and the combined interworking of these apparatus have numerous advantages some of which have been described above and others of which are inherent in the various apparatus and there combinations. In particular, a modular chemical analysis system 10 is provided which minimizes if not eliminates human contact with the sample serum and which provides an automatic means for obtaining the desired test results in a very short period of time.

Also from the foregoing description it will be apparent that obvious modifications and variations can be made to the system and apparatus of the invention without departing from the teachings of the invention. Accordingly, the scope of the invention is only to be limited as necessitated by the accompanying claims.

What is claimed is:

1. An automatic nephelometer apparatus comprising a sampling station;
a transporter for transporting sample cup cartridges in a predetermined path past said sampling station, each cartridge having a plurality of sample cups therein, and each cup containing a liquid particulate suspension;
a flow cell;
valveless fluid means for withdrawing a quantity of liquid from a selected one of said sample cups at said sampling station and for moving the quantity of liquid into said flow cell;
a source of coherent light;
means for directing coherent light through said flow cell;
means for selectively detecting the light scattered by the liquid particulate suspension and for producing a corresponding value therefor;
means for removing said quantity of sample liquid from said flow cell;
sample immunization means for cleaning all exterior and interior surfaces of said withdrawing means contacting said sample liquid and all of the interior surface of said flow cell to a level exceeding that contacted by said sample liquid particulate suspension;
means for identifying each sample liquid particulate suspension and means for storing such identification along with the light scattered value; and
programmable control means containing a plurality of accessible storage locations, for controlling operation of said nephelometer apparatus by controlling the activation of said transporter, operation of said fluid withdrawing means, operation of said coherent light means, operation of said scattered light detection means, operation of said cleaning means and operation of said identifying and storing means, at predetermined times and in a predetermined sequence.

2. The apparatus of claim 1 wherein said source of coherent light is a laser, said means for selectively detecting the light scattered includes at least one limiting aperture positioned to allow passage of scattered light at some predetermined angle relative to the incident beam to refine the scattered light for measurement and a photomultiplier tube to measure the intensity of the selected scattered light.

3. The apparatus according to claim 2 wherein said means for withdrawing sample liquid from said sample cup includes a sipping device comprising a hollow probe, means for moving said hollow probe up and down out of and into a sample cup located at said sampling station, a first pump fluidly coupled to said probe and an operating mechanism for said first pump controlled by said control means and operable to cause said first pump to aspirate the quantity of sample liquid from a sample cup when said probe is inserted therein and move said sample liquid to said flow cell.

4. The apparatus according to claim 3 wherein said first pump is fluidly coupled to one side of said flow cell and said probe is fluidly coupled to the other side of said flow cell.

5. The apparatus according to claim 4 wherein said cleaning means includes a cleaning station and a wash bowl at said cleaning station and said sipper device further includes means for moving said probe in a horizontal direction between a position over a sample cup and a position over said wash bowl and said up and down moving means is operable to move said probe into and out of said wash bowl and said first pump operating mechanism is operable to move wash fluid into and out of said probe.

6. The apparatus according to claim 5 wherein said cleaning means includes a second pump, a wash fluid reservoir fluidly coupled to said second pump, a fluid coupling between said second pump and said wash bowl, and an operating mechanism for said second pump controlled by said control means for transferring wash fluid from said reservoir to said wash bowl at predetermined times.

7. The apparatus according to claim 6 wherein said operating mechanisms for said first pump and said second pump are one and the same and such operating mechanism is mechanically coupled to both pumps to operate same in tandem.

8. The apparatus according to claim 7 wherein said operating mechanism has a reciprocal motion and includes stroke detecting means for limiting movement of a pump piston in each of said first and second pumps to one of five pump piston strokes of differing lengths, the first stroke being a very short "draw" stroke for aspiration of air into said probe, the second stroke being a continuation of the "draw" stroke and having a length sufficient for aspirating sample liquid from a sample cup into said probe and up to a predetermined level into said flow cell, said second pump being operated at the same time to draw a quantity of wash fluid from said reservoir, a third stroke being an "eject" stroke having a length greater than the sum of the first and second stroke lengths for ejecting all of the quantity of sample liquid from said flow cell and said probe back into the sample cup and at the same time to cause said second pump to eject wash fluid into said wash bowl at said wash station, the fourth stroke being a "draw" stroke and having a length greater than the sum of said first and second strokes for aspirating wash fluid into said probe and into said flow cell above the level reached by the quantity of sample solution in said flow cell and at the same time to cause said second pump to draw wash fluid from said reservoir, and the fifth stroke being an "eject" stroke and having a length greater than said fourth stroke to ensure that all of said wash fluid is ejected from said flow cell and probe while at the same time wash fluid is ejected by said second pump into said wash bowl and around the lower end of said probe to wash the outside of said probe while the wash fluid inside said probe is being ejected therefrom into said wash bowl.

9. The apparatus according to claim 8 wherein said means for aspirating a small amount of air simultaneously operates a cleaning mechanism to withdraw into a wash pump some wash fluid from a wash reservoir, said means for returning said withdrawing means also simultaneously initiates wash fluid to be delivered from said wash pump to a wash bowl at a wash station adjacent to said sampling station, and said electronic circuitry therein further comprises sequentially activated means, responsive to the activation of said means for repositioning said withdrawing means and returning said sample liquid, for performing the following functions before said means for indexing is activated;

moving said sample solution withdrawing means to said wash station and inserting a probe of said withdrawing means into said wash bowl at said wash station, aspirating wash fluid into said withdrawing means and moving said fluid into said flow cell above the level reached by the sample liquid drawn into said flow cell, operating simultaneously said wash pump and a sampling aspirating pump to eject the wash fluid from said flow cell and said probe into said wash bowl and simultaneously eject wash fluid into said wash bowl to wash the outside of said probe, operating said sample withdrawing means to move said probe to its initial sampling position.

10. The apparatus according to claim 2 wherein said programmable control means includes a programmed computer having electric circuitry therein connected so as to comprise sequentially activated means for performing the following sequence of functions:

(1) indexing of said transporter to move a sample cup into a sampling position at said sampling station,
(2) aspirating a small amount of air into said withdrawing means,
(3) moving said withdrawing means into said sample cup,
(4) aspirating a predetermined quantity of sample liquid from the sample cup by said withdrawing means into said flow cell,
(5) disabling of said light detection means to calibrate measuring circuitry associated therewith,
(6) enabling and operating said light detection means to detect the relative light scattered (R.L.S.) and to determine the minimum R.L.S. signal value during a pre-programmed time interval,
(7) transferring the identifying number of the sample solution, the sample solution concentration value, if known, and the R.L.S. value, to storage locations in said computer,
(8) repositioning said withdrawing means to its starting position and returning said sample liquid to the sample cup, and
(9) indexing of said transporter to place the next sample cup in a sampling position.

11. The apparatus according to claim 10 wherein said programmed computer includes circuitry connected to activate a predetermined sequence of means for performing operations on four different types of solutions, a referenced blank solution containing a known liquid sample with known concentration of the substance and a diluent, an unknown blank solution containing an unknown liquid sample with an unknown concentration of the substance and diluent, a reference test solution having the known liquid sample with a known concentration of the substance and a reagent, and an unknown test solution having the unknown liquid sample with an unknown concentration of the substance and a reagent, said predetermined sequence of means for performing operation steps being activated automatically and comprising means for:

processing a plurality of referenced blank solutions at maximum gain for said sensing means with operation functions (1)–(9) set forth in claim 10, processing a quantity of unknown blank solutions at maximum gain with functions (1)–(9) set forth in claim 10, storing all blank solution values in memory circuitry in said computer in a predetermined order, drawing of a quantity of the first reference test solution into said flow cell, adjusting detection means until the first reference test value measured by detection means is in the operating range of the measuring portion of said detection means, storing said adjustment in memory as percentage of maximum gain that is needed to place first reference test value in optimum range of measuring portion of sensing means, processing a predetermined plurality of test solutions according to functions (1)–(9) set forth in claim 10, subtracting from each R.L.S. reference test value of its corresponding R.L.S. blank value multiplied by the adjustment as a percentage of maximum gain to obtain corrected R.L.S. test values, forming a domain of independent variables comprising corrected R.L.S. reference test values and corresponding known concentration values from computer memory and inputing said domain into a polynomial regression curve fit program to obtain curve fit parameters, processing the plurality of unknown test solutions using functions (1)–(9) set forth in claim 10 to derive R.L.S. values for each unknown test solution and inputing said derived R.L.S. values into said polynomial regression curve fit equation with previously obtained curve fit parameters to obtain a calculated concentration value indicative of the concentration of the substance in the unknown test solution, visually displaying the unknown sample solution numbers and the calculated concentration values for the unknown sample solution numbers; and resetting said apparatus and returning said withdrawing means to its beginning position to enable processing a new assay with a choice of new blank solutions or utilizing same R.L.S. blank solution values stored in computer memory.

12. The apparatus according to claim 4 wherein said flow cell comprises a generally cylindrical cuvette with conically shaped tapered end portions which connect with respective fluid conduits at each end thereof.

13. A modular nephelometer system comprising:

a first module for preparing sample liquid particulate suspensions from specimen solutions, a second module coupled to and accepting prepared samples from said first module comprising a nephelometer apparatus including a stationary flow cell, means for moving sample liquids into and out of said flow cell, laser means for generating and passing coherent light through said flow cell and means for selectively detecting and measuring the relative light scattered (R.L.S.) by the sample liquid in said flow cell, a third module coupled to said first and second modules including means for receiving signals from and directing control signals to said first and second modules, comprising a microprocessor/calculator having a stored program and for actuating and controlling the sequence of operations of said first module and said second module and for receiving detected R.L.S. values from said second module and means for comparing with predetermined concentration values of those solutions from which R.L.S. values were obtained to obtain concentration values from said R.L.S. measurements for said sample liquid particulate suspensions.

14. The modular nephelometer system of claim 12 wherein said sample liquid particulate suspension preparation apparatus comprises a sample preparation station, a transporter for transporting sample cup cartridges, each having a plurality of sample cups therein, past said sample preparation station, a given number of the sample cups having a sample liquid therein and an equal number of empty cups being aligned therewith, means for metering a given amount of diluent or reagent and for dispensing same at said sample preparation station into selected ones of the empty sample cups, means for withdrawing a precise minute amount of sample liquid from each of those cups having sample liquid therein at said sample preparation station and for dispensing said precise minute amount of said sample liquid into selected ones of the empty sample cups aligned therewith, means for washing all interior and exterior surfaces of said sample withdrawing and dispensing means contacting said sample liquid between dispensings of said samples.

15. The apparatus according to claim 14 wherein said sample liquid withdrawing and dispensing means includes a syringe with a syringe piston and a syringe probe movably mounted at said sample preparation station.

16. The apparatus according to claim 15 wherein said withdrawing and dispensing means includes means for moving said syringe probe up and down and means for causing said syringe piston to aspirate a precise minute quantity of sample liquid when said syringe is in a down position with the syringe probe immersed in sample liquid in a sample cup.

17. The apparatus according to claim 16 wherein said withdrawing and dispensing means includes means for moving said syringe back and forth in a generally horizontal plane when it is in an up position and between a position over a sample cup containing sample liquid and a position over an aligned empty sample cup.

18. The apparatus according to claim 17 wherein said control means includes electric circuitry for causing said withdrawing and dispensing means to move said syringe probe into said wash bowl after said precise minute quantity of sample liquid has been aspirated into the syringe probe but before the syringe probe is positioned over a sample cup to dispense the precise minute amount of sample liquid into an empty sample cup thereby to remove any sample liquid from the exterior of said syringe probe to ensure the dispensing of a precise minute amount of sample liquid into the sample cup.

19. The apparatus according to claim 18 wherein said cleaning means includes a wash station having a wash bowl therein adjacent said sample preparation station and said control means includes means for causing said back and forth moving means to move said syringe probe over said wash bowl where it can be dipped therein and for causing said syringe piston to aspirate cleaning liquid into said probe and then dispense cleaning liquid therefrom to wash the interior of said syringe probe.

20. The apparatus according to claim 19 including means for draining said wash bowl at predetermined times with operation of said draining means being controlled by said control means.

21. The apparatus according to claim 20 wherein said cleaning means includes, in addition to said wash bowl, a drain conduit from said wash bowl, a drain reservoir positioned below said drain conduit, a valve in said drain conduit operated by said control means, a wash fluid reservoir, a pump fluidly coupled to said reservoir for withdrawing wash fluid from said reservoir through a valve and a conduit from said valve to said wash bowl, said control means being operable to cause said pump to remove a quantity of wash fluid from said reservoir in one stroke and for dispensing said wash fluid taken into said pump into said wash bowl on a reverse stroke.

22. The apparatus according to claim 21 wherein said metering and dispensing means for metering a given amount of reagent or diluent and dispensing the metered amount of reagent or diluent into an empty sample cup includes a tubing having an open outlet end and extending from said metering and withdrawing means to a position over the path of travel of the empty sample cups with said outlet end positioned over said path of travel.

23. The apparatus according to claim 14 wherein said transporter includes a conveyor mechanism having a conveyor which moves in a closed path and means on said conveyor for detachably securing each one of the cartridges onto the top surface of said conveyor in a manner such that each cartridge is moved in an upright position and along a line parallel to the long axis thereof as it passes said sample preparation station and said apparatus further includes an adapter having means for detachably engaging said detachable securing means on said conveyor on a lower surface of said adapter and said adapter having means on the upper surface thereof for mounting thereon two sample cup cartridges in parallel relationship and with each sample cup in one cartridge aligned with a like sample cup in the other cartridge such that said conveyor mechanism of said transporter can move a pair of aligned cartridges mounted on said adapter past said sampling station.

24. The apparatus according to claim 23 wherein said adapter has a depending lower elongate portion having a width approximately the same as the width of one of the sample cup cartridges with openings therein adapted to be received over and on upstanding lugs on said conveyor which form said means for detachably securing a cartridge on said conveyor and said adapter having a wider upper portion with two pairs of aligned upstanding lugs on the upper surface thereof each pair of lugs being adapted to have received thereon socket means formed in the underside of a sample cup cartridge.

* * * * *